US008512754B2

(12) United States Patent
Needham

(10) Patent No.: US 8,512,754 B2
(45) Date of Patent: Aug. 20, 2013

(54) STABILIZED PRODUCTS, PROCESSES AND DEVICES FOR PREPARING THE SAME

(76) Inventor: David Needham, Durham, NC (US)

( * ) Notice: Subject to any disclaimer, the term of this patent is extended or adjusted under 35 U.S.C. 154(b) by 0 days.

(21) Appl. No.: 13/199,573

(22) Filed: Sep. 2, 2011

(65) Prior Publication Data
US 2012/0082715 A1 Apr. 5, 2012

Related U.S. Application Data

(60) Continuation of application No. 11/796,451, filed on Apr. 27, 2007, now Pat. No. 8,013,022, which is a division of application No. 11/007,104, filed on Dec. 8, 2004, now abandoned.

(60) Provisional application No. 60/527,810, filed on Dec. 8, 2003, provisional application No. 60/619,863, filed on Oct. 18, 2004.

(51) Int. Cl.
*A61K 9/14* (2006.01)
*A61K 9/16* (2006.01)

(52) U.S. Cl.
USPC .......... 424/489; 514/938; 514/937; 424/94.1; 424/1.49; 424/130.1; 424/150.1; 424/490; 424/491; 435/183

(58) Field of Classification Search
USPC ................ 435/183; 514/938, 937; 424/94.1, 424/1.49, 130.1, 150.1, 490, 489, 491
See application file for complete search history.

(56) References Cited

U.S. PATENT DOCUMENTS

| 5,935,588 A * | 8/1999 | Afriat et al. .................... 424/401 |
| 2006/0024379 A1* | 2/2006 | Brown et al. ................. 424/490 |

\* cited by examiner

*Primary Examiner* — Nathan Bowers
(74) *Attorney, Agent, or Firm* — Denise L. Mayfield

(57) ABSTRACT

A composition comprising a glassified, stabilized particle preparation having a low water activity (between about 0.1 and 0.9) is provided. The preparations provide improved products with enhanced storage stability, less expensive cost of processing, and extended shelf life. The glassified, stabilized particle preparations are particularly efficacious in the preparation of perishable products, especially pharmaceutical agents, such as human blood and blood products (e.g., red blood cells). A single emulsion process comprising a 2-phase system for preserving food and pharmaceutical products is also provided. Stabilized biological products as glassified beads are also provided, as well as a method for rehydrating and/or reconstituting the glassified beads to provide useful and fully active reconstituted and/or rehydrated materials is also presented.

18 Claims, 4 Drawing Sheets

STABILIZED PRODUCTS, PROCESSES AND DEVICES FOR PREPARING THE SAME

The present application claims priority to U.S. Provisional Application Ser. No. 60/527,810, filed Dec. 8, 2003, to U.S. Provisional Application Ser. No. 60/619,863, filed Oct. 18, 2003. U.S. Ser. No. 11/007,104 (filed Dec. 8, 2004) and U.S. Ser. No. 11/796,451 (filed Apr. 27, 2007) the present application is a continuation of U.S. application Ser. No. 11/796,451, filed Apr. 27, 2007, which is a divisional application of U.S. Ser. No. 11/007,104, filed Dec. 8, 2004.

FIELD OF THE INVENTION

The invention relates to the field of processing and storage/preservation devices, as devices useful in the collection, processing, dehydration, and storage of perishable materials, including food products, pharmaceuticals and biological products, especially pharmaceuticals and biological products are provided. The present invention in particular aspects also relates to the field of stabilized products, such as preserved food, pharmaceuticals and biological products, including blood and blood components, and to storage devices suitable for storing and transferring these stabilized products. The invention also relates to methods of processing perishable food, pharmaceutical and biological products, especially red blood cells, plasma, and platelets, using a process that provides for reducing the hydration level of a material to a level below its native state of hydration, but which does not destroy and/or significantly reduce the nutritional, biological and/or pharmacological activity level of the material upon rehydration to its native state. The invention also relates to the fields of processes for increasing the shelf life of a perishable material, such as food, pharmaceutical and biological products, as well as to methods of formulating, distributing and/or administering these stabilized products.

BACKGROUND OF THE RELATED ART

The water activity ($a_w$) of a material is primarily dependent on the characteristic water content of the material in its native state and on the nature and kind of components that comprise the material. The manner in which the components of the hydrated material interact with water is also relevant to water activity. In regard to certain biologically important products, such as blood component products (red blood cells, platelets, plasma, hemoglobin, etc.), the water activity level greatly affects the susceptibility of the material to the growth of bacteria and molds.

It has been found that organisms struggle to grow at water activities less than 0.9. Enzyme activity has also been reported to decrease significantly below a water activity of about 0.9. Therefore, a major goal in preserving cellular and/or potentially perishable materials and an aspect of the present invention is to achieve a reduction of the water activity of the sample to at least about 0.9 or below. In this manner, microbial growth may be reduced and/or inhibited, and enzymatic activity in the material may be reduced.

Maintenance and distribution of adequate perishable supplies of foodstuffs, pharmaceuticals and biological products, such as blood and blood components, have historically constituted a significant problem in societies around the world.

In the case of perishable and necessary biological products, such as blood, a recent study reports that current methods of storing blood products compromises the blood unit in such a way as to increase risk of serious side-effects in coronary patients. In one study (Relationship of Blood Transfusion and Clinical Outcomes in Patients with Acute Coronary Syndromes, Rao et. al., JAMA, 2004, 1555-1562), 24,112 patients characterized as having acute coronary syndromes, and grouped according to whether they received transfusions of red blood cells during hospitalization, were examined. Of these patients, 2,401 (10.0%) received at least one stored red blood cell unit. This group was reported to have a higher 30-day mortality and a higher occurrence of myocardial infarction than the group that received no transfusion. The reason for this increased mortality and morbidity is unclear, but may at least in part be due to a phenomenon known as "storage lesion" formation. Specifically, the stored red blood cells used in these transfusions may have had altered nitric oxide biology and reduced 2,3, diphosphoglycerate levels, resulting in higher oxygen affinity hemoglobin, as well as an increase in inflammatory mediators.

This study illustrates the profound effect that the phenomena known as "storage lesions" associated with conventional collection and storage has on a large percentage of coronary patients, and the urgent need for improving these techniques.

Using conventional collection techniques, the maximum storage time for red blood cells at 1-6° C. is 42 days. During this relatively short storage time, storage lesions develop that significantly affect the function of RBCs. The RBC changes that occur as a consequence of the formation of storage lesions include decreased 2,3-diphosphoglycerate, decreased ATP, increased potassium, decreased cell viability, and decreased pH. The shelf life of RBCs is determined as a measure of the number of days a collected unit of RBCs can be stored and retain a viability of at least 75% of the number of infused RBCs in circulation in the patient 24 hours after transfusion of the stored unit. Using conventional preparation and storage methods, the shelf life of a unit of whole blood is about 21 days.

The current shelf life of red blood cells, leukoreduced (having a residual leukocyte content less than $5\times10^6$) is about 42 days. The shelf life for washed red blood cells and for deglycerolized red blood cells is about 24 hours. The shelf life of fresh frozen plasma is one-year. The shelf life for leukoreduced random donor platelets as well as for leukoreduced single donor platelets (apheresis platelets) is about 5 days. (American Red Cross, Hospital Resource Center, Products, December 2004).

In addition to difficulties associated with the relatively short shelf life of stored blood products, the current requirement that these units be stored under refrigerated conditions still leaves blood supplies subject to potential bacterial contamination. Even an incremental increase in the standard shelf life and/or increase in the range of acceptable storage conditions/temperatures required to maintain viable biological and pharmaceutical products would present a significant advantage in these industries.

Fresh frozen plasma (FFP) is primarily indicated for patients with active or threatened bleeding who need short-term correction of coagulation factor deficiencies. For the average adult, each unit raises clotting factor levels 2-3%. More than two units are usually needed for replacement therapy. FFP alone should not be used for volume replacement. Each unit of FFP contains 200 to 225 ml of plasma derived from a single whole blood unit, and is frozen at −18° C. or colder in order to preserve the labile factors V and VIII at hemostatic levels. FFP also contains a variety of stable proteins involved in the complement and fibrinolytic systems, in the maintenance of oncotic pressure and in the modulation of immunity. Units of FFP are labeled specifically for the ABO blood type of the donor from whom they are prepared.

Each unit is also tested for the presence of syphilis, hepatitis B, hepatitis C, HTLV-1, HIV-1 and HIV-2. This testing and labeling protocol is also characteristic of the procedure used for red blood cells and platelets.

Another major indication for FFP is as a replacement therapy for documented single or multiple coagulation factor deficiencies. Documentation may be by direct measurement of clotting factor levels or by prolongation of the prothrombin time (PT) or activated partial thromboplastin time (PIT). Other indications are for thrombotic thrombocytopenic purpura (TTP) and during massive blood transfusion (>1 blood volume within 24 hours). FFP may be used for patients having a coumadin overdose or that suffer from hereditary antithrombin III deficiency or hereditary protein C deficiency. However, prothrombin complex or antithrombin III concentrates may be the therapy of choice depending on availability and the specific clinical situation. The use of FFP for the treatment of selected immunodeficiencies has been replaced by intravenous immunoglobulin preparations.

The dose of FFP for coagulopathies should be determined by the amount required to adequately replace deficient clotting factor levels or to correct the PT and APTT. The average adult will require at least 3-4 units of FFP as replacement therapy. Administering 3-4 units of FFP will usually raise levels of each clotting factor level into the hemostatic range, which is 20-40% of normal depending on the clotting factor or factors involved.

As with any blood product, infusion of FFP requires a standard blood administration set. If the patient's circulatory status permits, FFP may be rapidly infused over 20-30 minutes. Depending on the blood type of the donor, FFP may contain A or B antibodies. Therefore, type specific or type compatible plasma is required. Thawing of FFP requires 30 minutes or more, and the unit must be administered within six hours of thawing.

Problems associated with the use of stored blood products include allergic reactions and viral contamination. For example, allergic reactions occur in about 1% of patients receiving FFP. These allergic reactions usually consist of pruritus or hives, which typically respond to treatment with antihistamines. However, rare fatal anaphylactic reactions have been reported. Most of these reactions are related to a specific donor unit and do not preclude further FFP use. The risks of viral transmission from FFP are similar to those for red cells and platelets. However, there is probably no risk of transmission of CMV or HTLV-1 since these viruses require cellular vectors for transmission. Circulatory overload occurs in many patients receiving large amounts of FFP due to the typically high volume of this product that is administered. This particular disadvantage limits the use of high volume FFP administration for patients with cardiac disease.

A recent development in blood component products has been the commercial introduction of pooled FFP. Up to 2500 units can be collected and processed to constitute a "pool" of plasma. Pooled FFP is plasma that has been treated with a solvent detergent prior to freezing in order to reduce the possibility of viral transmission by eliminating envelope viruses. While the solvent/detergent treatment process inactivates lipid-enveloped viruses, the process does not inactivate non-enveloped viruses. Therefore, medical heath risk from exposure to parvovirus B19, hepatitis A, and yet unidentified pathogens that might contaminate the pool, continue to exist.

Pooled FFP product is sold and used extensively in Europe and other countries outside the United States. A major disadvantage of blood bank or commercial FFP is the need to insure maintenance of the frozen state during storage and shipping. This creates major logistical problems and increases shipping and storage expense to assure that the product remains frozen during distribution and until use.

Stored platelet components also suffer from the effects of storage lesions. Formation of these lesions result in the release of alpha and dense granules, morphological changes to the cytoskeleton, altered surface proteins including receptors related to activation and aggregation, and loss of membrane asymmetry. All of these changes are associated with procoagulant activities of platelets, and represent degradation of the stored platelet's capacity to function normally, as well as exposing the patient to components with potentially adverse, thrombotic side effects. In addition, storage at 20° C. does not prevent growth of pathogenic organisms, thus exposing the patient to potential infectious agents.

Because of the several technical storage, degradation, and physiological phenomenon to which important and perishable products are affected, especially blood products and pharmaceutical agents, a major unmet need continues to exist for a process and/or processing system that would stabilize and extend the shelf life of these commodities. Such a process would preferably reduce the need for blood product to be stored at −18° C. and/or extend the shelf life of these products after thawing/defrosting. Currently, it is necessary to maintain a cold-chain distribution system for blood products that is cost effective and that satisfies logistically time-sensitive distribution criteria.

A societal need continues to exist for a perishable product collection and storage technique that would eliminate and/or reduce the various medical, pharmaceutical, and food preservative associated issues noted herein. The presently disclosed invention addresses these and other significant deficiencies in the art.

BRIEF SUMMARY OF THE INVENTION

The present invention, in a general and overall sense, provides for stabilizing otherwise at least partially perishable products by removing and/or reducing the moisture/liquid present in the material. An advantage inherent to these products is that they are not exposed to any desiccant, absorbing material, polymer, or other foreign chemical.

In some embodiments, the products constitute compositions comprising a food product, pharmaceutical product, medical product, or any intermediate chemical, pharmacological, and/or biological reagent thereof, that has been processed so as to reduce water activity $a_w$. Particular embodiments of the medical products comprise compositions of blood or blood component products. By way of example these blood or blood component products comprise compositions of platelets, red blood cells (RBCs), hemoglobin, plasma, or any particular fraction and/or preparation of these blood components or products.

The invention provides in some aspects several devices and processing systems that may be used in the preparation, storage, and/or delivery of the various stabilized products described herein. Several designs of these devices and systems are provided herein at FIGS. 1-3, and are expected to provide a product having the improved characteristics described herein.

Device System 1—One particular embodiment of the device/system of the present invention is generally depicted in FIG. 1. In this embodiment, a System 1 is provided wherein a stabilized (partially dehydrated) product is retained in a separated compartment of the device after preparation, where it will remain until use. At the time the stabilized product is to be used, an appropriate kind and amount of reconstituting material (diluent and/or additive) may then be added to the stabilized product and used (i.e., delivered to a recipient, consumer and/or patient). In System 1, the devise 1 comprises a first compartment 2 and a second compartment 3, separated by a partitioning material 4.

The partitioning material 4 may comprise, by way of example, a membrane or series of membranes having a surface or a portion of a surface that is permeable to moisture and/or liquid components and small molecular weight size particles. In some embodiments, the partitioning material 4 will comprise a semi-permeable membrane that permits the passage of moisture and/or liquid out of the material of interest being processed. The partitioning material may be further described as preventing the influx of moisture, liquids, or other materials into the material being processed (dehydrated). Specifically, as part of the device configuration as described herein at FIGS. 1 and 2, the semi-permeable partition (such as a membrane) 4 will permit the passage of moisture and/or liquid out of the compartment containing the material of interest being processed (Compartment 2), but will prevent the passage of moisture and/or other material or liquid into the compartment containing the material of interest being dehydrated. Hence, III some embodiments, the moisture component and/or liquid component of any material of interest being processed will pass into and remain in a separate compartment (Compartment 3, FIG. 1 and FIG. 2). In some embodiments, the moisture and/or liquid will be absorbed by an absorbent desiccating material (i.e., a polymeric material) contained in the separate compartment (Compartment 3), away from the processed and stabilized material.

The partitioning material 4 will also prevent the passage of absorbing and/or desiccating material or chemical from contacting the material being processed. This is a particularly important advantage of the present process, as any potentially compromising chemical effects of the desiccating/absorbing materials or any by-products formed as a consequence of the desiccating and/or moisture removing procedure will remain away and separate from the processed material. It is anticipated that this will provide a much purer and concentrated processed product that is essentially free of any material that is other than the processed material itself or its components.

Referring now to FIG. 1, a compartment 2 is provided that comprises an inlet port 5. The inlet port 5 comprises a valve, particularly a one-way valve (V1), that prevents the flow of material out of the compartment 2, and that only permits material to enter into the compartment 2. Compartment 2 also may comprise, in some embodiments, an additional inlet port 6. Inlet port 6 may comprise a valve, in particular a one-way valve (V2) that will permit the flow of material into the compartment 2. It is anticipated that this inlet port 6 will facilitate the flow of appropriate diluents, such as saline, or other appropriate or desired material reconstitution fluids, including additives (such as AS-1, AS-3 and AS-5), into the compartment 2. In this fashion, a processed material may be rehydrated when needed for use. This embodiment of the device eliminates the need for a separate storage compartment for the processed material once the material of interest has been processed and/or stabilized to a reduced water activity level (less than about 0.9). It is anticipated this self-contained system will be very economical and convenient to use.

Compartment 2 in some embodiments of the invention will preferably comprise an outlet port 7. In use, it is anticipated that outlet port 7 will provide for the flow and/or expulsion of the processed material in its dehydrated form, or the reconstituted processed material in its rehydrated form, out of compartment 2. The outlet port 7 may further comprise a valve, in particular a one-way valve (V3). The valve is envisioned to provide for the flow of material out of the compartment 2, and will prevent the flow of material into the compartment 2.

Compartment 3 of the device will comprise in some embodiments an inlet port 8. Compartment 3 will preferably include an adequate volume of a moisture absorbing material 14, such as a polymer or other moisture-absorbing material. Inlet port 8 is anticipated to be useful for adding additional and/or unexpended absorbent material into the compartment 3. Inlet port 8 will also include a valve, particularly a one-way valve (V4), that will permit material to come into the compartment 3, and will prevent material from leaving compartment 3. Compartment 3 of the device, in some embodiments, may in additional embodiments comprise an outlet port 9. Outlet port 9 is anticipated to provide an outlet port from which expended absorbent materials may be purged out of the compartment 3. Outlet port 9 will in some embodiments comprise a valve, preferably a one-way valve (V5), that will permit material/liquid to evacuate the compartment 3, and will prevent any material/liquid from entering into the compartment 3.

In some embodiments, the device 1 may further comprise a purged/expended material storage and collection unit 10. In these embodiments of the System 1, the outlet port 9 from compartment 3 will be connected to said storage and collection unit 10. The storage and collection unit may in some embodiments further comprise an outlet port 11. Outlet port 11 may optionally and additionally comprise a one-way valve (V6). The one-way valve V6 of the outlet port 11 will provide for the removal of the stored purged/expended material from the storage and collection unit 10.

In use, it is anticipated that the processed material having a reduced water activity less than about 0.9 will be stored in compartment 2 until use of the processed material is desired. When the processed material is needed for use, an appropriate diluent and/or additive may be added to the compartment 2 through the above described inlet port 6. In the case of a sample of processed (partially dehydrated, reduced $a_w$) red blood cells, for example, the processed red blood cells would be resuspended in an appropriate volume of sterile saline through the addition of saline to the compartment 2 though inlet port 6.

Device System 2—Another embodiment of the device/system of the present invention is generally depicted in FIG. 2. In this embodiment, a System 2 is provided that constitutes a system whereby the processed (stabilized, reduced $a_w$) product is removed from the processing apparatus after partial dehydration, and then reconstituted with the appropriate amount of reconstituting material in a secondary storage container system 21. In this system, the stabilized product is to be stored and/or retained in a compartment 22 of the secondary storage system 21 until it is needed for use. At that time, the stabilized/processed product is reconstituted with an appropriate dilute/fluid and delivered to the recipient, consumer and/or patient.

In System 2, the devise 1 comprises a first compartment 2 and a second compartment 3, separated by a partitioning material 4. The compartment 2 of the device comprises an inlet port 5. The inlet port 5 comprises a valve, particularly a one-way valve V1, that prevents the flow of material out of the compartment 2, and that only permits material to enter into the compartment 2.

The partitioning material 4 may comprise, by way of example, a membrane or series of membranes having a surface or a portion of a surface that is permeable to moisture and/or liquid components and small molecular weight size particles. In some embodiments, the partitioning material 4 will comprise a semi-permeable membrane that permits the passage of moisture and/or liquid out of a material of interest being processed according to the methods described herein. The partitioning material may further be described as not being permeable to moisture, liquids, or other materials in the compartment 2 or to the material that has been processed according to the process described herein. Specifically, as part of the device configuration as described herein at FIG. 2, the semi-permeable membrane 4 will permit the passage of moisture and/or liquid out of the compartment containing the material of interest being processed (Compartment 2), and will prevent the passage of moisture and/or other material or liquid into the compartment containing the material of interest (Compartment 2). Hence, in some embodiments, the moisture component and/or liquid component of any material of interest being processed will remain in Compartment 3.

The partitioning material 4 will also prevent the passage of any absorbing and/or desiccating material or chemical from contact with the material of interest being processed in compartment 2. Among others, this presents a particular advantage in that any potentially compromising chemical effects of the desiccating/absorbing materials or any by-products formed as a consequence of the desiccating and/or moisture removing procedure, such as chemicals and/or other non-product substances, will remain away and separate from the processed material product. It is anticipated that this will provide a much purer and concentrated processed product that is essentially free of any material that is other than the processed material itself or its components.

Compartment 2 in some embodiments of the invention will preferably comprise a second outlet port 7. In use, it is anticipated that outlet port 7 will provide for the flow and/or expulsion of the partially dehydrated and processed material out of compartment 2. The outlet port 7 may further comprise a valve, in particular a one-way valve (V3) that will permit the passage of material out of the compartment 2 and will prevent the entry of material into the compartment 2.

As part of the System 2 depicted in FIG. 2, the outlet port 7 will be connected to a secondary storage container system 21. The secondary storage container system 21 in some embodiments of the invention may be described as comprising a processed dehydrated sample container 22, a diluent containing/holding compartment 23, and a partition 24 that separates the processed dehydrated material container 22 and the dilute/additive holding compartment 23. It is anticipated that the diluent containing/holding compartment 23 will include a sufficient volume of an appropriate diluent, such as saline, and/or additive (AS-1, AS-2, AS-5) to resuspend, for example, a processed volume of red blood cells. The partition 24 will further comprise an inlet port 26. Inlet port 26 will preferably include a valve, particularly a one-way valve V7 that will provide for the flow/addition of an appropriate amount and kind of a desired diluent into the dehydrated material contained in compartment 23. The valve V7 will prevent the flow of diluent and/or additive out of compartment 23. The diluent containing/holding compartment 23 may comprise in even more particularly defined embodiments, an outlet port 27.

The devices and compartments/components thereof as herein described may be fabricated using any number of know fabricating materials suitable for the processing and storage of pharmaceutical, food and/or biological products. By way of example, such materials include plastics, acrylics, polymers, cellulose-based materials, cellulose acetate, fiberglass components, or any other material designed such as to accommodate the containment of a material having a liquid component. Preferably, the material will be capable of withstanding sterilization, particularly in the case of biological and pharmaceutical products.

The Process—Process I (Particle and/or Glassified Bead Formulation)—The invention provides in some embodiments a method/process for preparing a stabilized material. It is envisioned that this particular process will be particularly suitable for the processing of pharmaceuticals, biological products, and food products. In particular applications of the process, it is envisioned that the method may be useful in the preparation of stabilized preparations of biological and/or pharmaceutical products and components thereof. By way of example, such products include but are not limited to hemoglobin, proteins, polysaccharides, nucleic acids, water-soluble oil-insoluble organic chemicals and inorganic chemicals.

In some embodiments, the material of interest is prepared so as to form a material having reduced moisture level or water activity ($a_w$). The processed materials will in some embodiments of the invention be in the form of a particulate substance and/or micro- or nano-beads. The beads may be further defined at least in some embodiments of the invention as glassified micro beads. The micro beads may be stored for relatively long periods of time until the desired use of the material so processed, and then rehydrated using the addition of an aqueous solvent.

In a particular embodiment, the process for stabilizing a material to form a stabilized product having a reduced water activity less than about 0.9 may be described as comprising a two (2) phase system. This two (2) phase system may be further described as comprising an aqueous phase and a non-aqueous phase, the process being more particularly described as comprising preparing a first aqueous phase comprising an aqueous solution of the material of interest in a sufficient volume of a solution, such as water. The material of interest is to be included in this first phase solution at a relatively high concentration level. A second phase is then to be prepared comprising dispersing the aqueous phase solution in a non-aqueous suspending solvent (such as decamp, to form a water-in-oil emulsion, then agitating and/or mixing the water-in-oil emulsion so as to provide for the formation of particles of the stabilized product, and then collecting the stabilized product particles. The stabilized product particles may be further defined as comprising a stabilized material having a water activity level ($a_w$) less than about 0.9, between about 0.1 to about 0.9, or about 0.3 to about 0.9.

The process may further include an additional step whereby the stabilized product particles may be resuspended and reformulated for use. In this process, the additional step is made of suspending the particulate material in a sufficient volume of an appropriate diluent and/or other liquid, such as water. In this manner, the reconstituted stabilized product will be released into the aqueous phase to provide the reconstituted product.

In particular embodiments, the material of interest that may be processed in this manner is a pharmaceutical or biological product. By way of example, the biological material may comprise blood components, particularly hemoglobin. In this embodiment, the hemoglobin may be described as forming a stabilized composition of glassified micro beads.

The Process—Process II (Reduced Water Activity ($a_w$) Preparation (Non-Glassified). It is envisioned that this particular process will be particularly suitable for the processing of food, pharmaceutical and biological products. By way of example, such products include biological products, including blood products. By way of example, such blood products include but are not limited to red blood cells, platelets, plasma, as well as other biological materials, including but not limited to viruses, bacteria, yeast, moulds, mammalian stem-cells, hematopoetic progenitor cells, and other types of eukaryotic cells of vertebrate or invertebrate origin.

The Process II as described herein possesses many advantages over conventional methods. Among others, one such advantage is that the material of interest, is never exposed to any foreign and/or non-native product material as part of the process. Such provides an additional safeguard against contamination from foreign chemical and/or biological materials.

In some embodiments of the Process 2, the process comprises the steps of placing the composition comprising a hydrated or partially hydrated material of interest in a device comprising a first container and a material (i.e., barrier membrane) permeable to moisture and/or liquid, and drawing out moisture and/or liquid that may be present in the material through the permeable barrier and out of the material being processed, so as to provide a stabilized material having a reduced water activity ($a_w$). The water activity level of the stabilized material is less than the water activity level of the material prior to processing, and may be describe more particularly as less than 0.9, or about 0.1 to abut 0.9, or about 0.3 to about 0.9. The processed and stabilized material may also be further described as essentially free of contact with any non-material components and/or chemical (i.e., desiccating) agents.

In the above method, the material to be processed comprises virtually any material having a moisture and/or liquid component. Examples of such materials include red blood cells, pharmaceuticals, platelets, plasma, viruses, bone marrow, progenitor cells or any fraction or component part thereof.

As used in the description of the present invention, the term "a" is intended to mean one or more.

Additional advantages, objects, and features of the invention will be set forth in part in the description which follows and in part will become apparent to those having ordinary skill in the art upon examination of the following or may be learned from practice of the invention. The objects and advantages of the invention may be realized and attained as particularly pointed out in the appended claims.

BRIEF DESCRIPTION OF THE DRAWINGS

The invention will be described in detail with reference to the following drawings in which like reference numerals refer to like elements wherein.

DETAILED DESCRIPTION OF PREFERRED EMBODIMENTS

Figure 1:
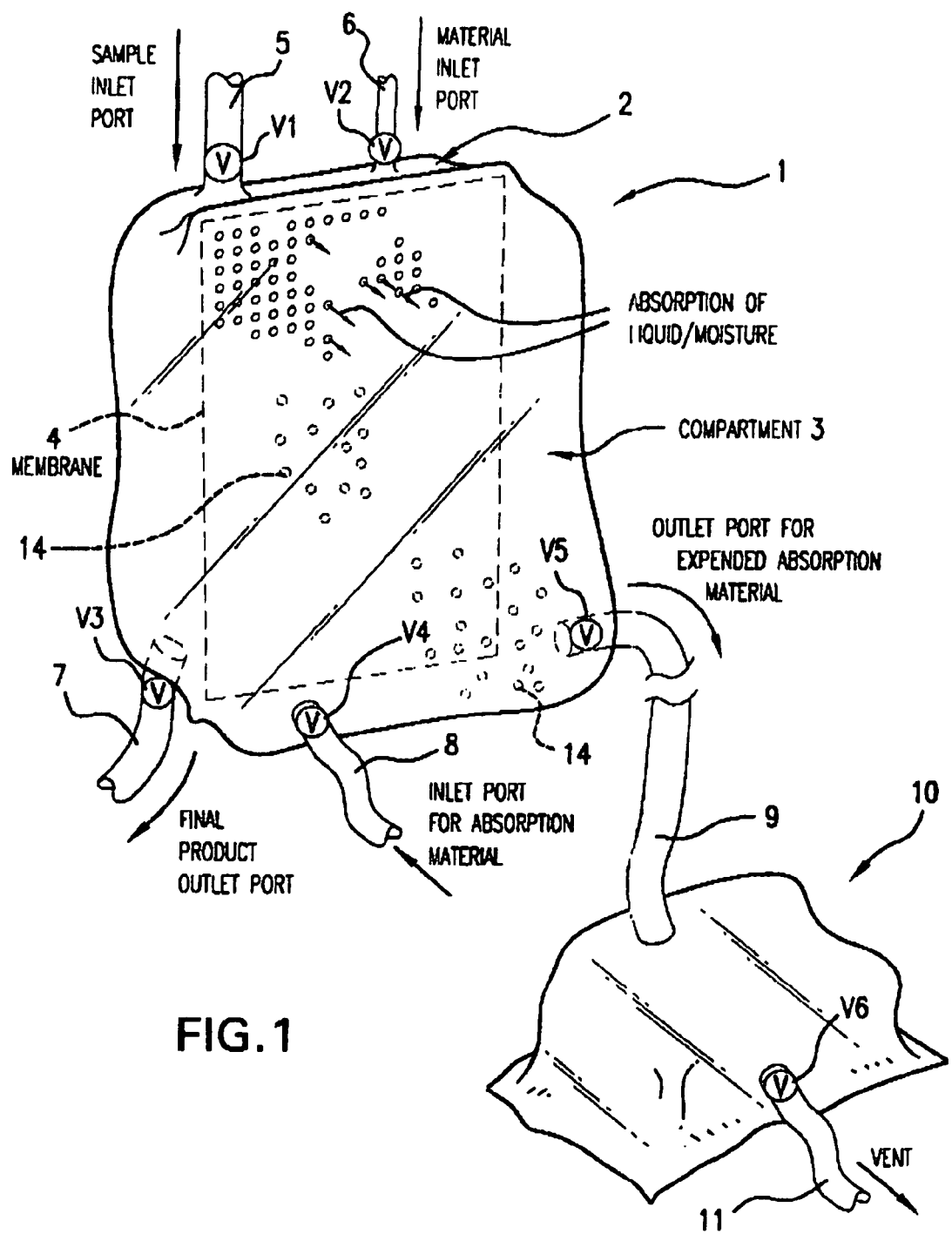
FIG. 1—Material Collection System and Device 1—material compartment/bag (2), absorptive compartment (3), semi-permeable partition/membrane (4), inlet port A (5), inlet port B (6), outlet port C (7), inlet port (8), outlet port (for removal of expended absorbed material) (9). One-way valves (V) at inlet port 5 (V1), inlet port 6 (V2), inlet port 8 (V4), outlet port 7 (V3) and outlet port 9 (V5). Expended (moisture-laden) absorptive material storage and removal unit 10, connecting with compartment 3 through inlet port 9. Outlet port 11 of said unit 10 having a one-way valve, V6.

The foregoing embodiments and advantages are merely exemplary and are not to be construed as limiting the present invention. The present teaching can be readily applied to other types of apparatuses. The description of the present invention is intended to be illustrative, and not to limit the scope of the claims. Many alternatives, modifications, and variations will be apparent to those skilled in the art. In the claims, means-plus-function clauses are intended to cover the structures described herein as performing the recited function and not only structural equivalents but also equivalent structures.

In some aspects, the invention provides a storage device that is useful, among other utilities, for the preservation and/or partial dehydration and reduction of water activity ($a_w$) level of a pharmaceutical, biological or food product material. In particular embodiments, the biological materials comprise the cellular elements of blood (primarily red cells and platelets) that may be stabilized through their dehydration, reduction in water activity, vitrification or induction of the glass or glass-like state. This is achieved through the principle of dialysis whereby polymeric materials, and in particular specialized polymers, absorb the liquid portion of blood cellular elements through a semi-permeable membrane.

In one aspect and/or embodiment of the inventive devise, the device comprises a compartment for storing the partially dehydrated material suspended in an aqueous solution; a separate compartment for storing the moisture absorbing material; and a moisture permeable material separating the two compartments such that water and moisture can be transported out of the material being processed to a compartment containing the moisture and/or water absorbing material. The moisture and/or water permeable material will in some embodiments comprise a membrane comprising a molecular pore size appropriate for permitting the passage of moisture and/or water molecules that are present in and/or around the material of interest, and at the same time, suitable for preventing the passage of particulate matter having a defined size there through.

In other embodiments, the processed material will be prepared so as to achieve a water activity ($a_w$) level of less than 0.90, 0.80, between about 0.10 to about 0.90, about 0.10 to about 0.85, about 0.15 to about 0.85, about 0.20 to about 0.90, about 0.25 to about 0.85, about 0.25 to about 0.8, about 0.25 to about 0.90, about 0.3 to about 0.9.

The moisture absorbing material may comprises any variety of commercially available materials, such as polyethylene glycols, dextrans, polyalcohols, polyacrylamides, starches, gums and others.

EXAMPLE 1

Multi-Phase Process for Preparing Stabilized Reduced Hydration Materials

The present example demonstrates the utility of the present invention for dehydrating compositions that are water-soluble and oil-insoluble. In particularly defined embodiments, the process provides for the production of glassified compositions. In the case of biological materials and products, a solid or semi-solid phase is provided that preserves essentially all of the biological activity of the composition as the composition contained prior to glassification. In some embodiments, the product comprises a protein, such as a composition of blood or blood components, particularly hemoglobin. It is envisioned that the presently described processes may also be used in the preparation and processing of pharmaceutical products, proteins, polysaccharides, nucleic acids, inorganic and organic chemicals, and the like.

In the present example, the protein composition being processed comprises hemoglobin, and the hemoglobin will be glassified to provide a preparation described herein as beads, specifically micro-beads.

As used in the description of the present invention, the term, "glassification" or "glass-like" is intended to be defined as non-crystalline formations of protein. In this state, damage and or decrease in biological integrity of the protein, such as hemoglobin protein, will not be significant, and in essentially all cases not more that a measurable loss of activity (i.e., oxygen carrying activity in the case of hemoglobin) compared to biological capacity prior to the partial dehydration, or glassification, process as described for the present invention.

Using the present two-phase micro system of glassification, a first phase is provided wherein the protein is prepared so as to form a micro droplet. This micro droplet first phase may then stored and later dissolved into a second phase at the time when the protein composition (hemoglobin) is to be used. To effect the transition of the micro droplet into the second phase, the micro droplet is dissolved into a relatively immisible excess phase. The first phase micro beads comprise the protein composition in micro glass beads of the protein, the protein existing in the micro glass beads in a reduced hydration state.

Advantageously, a protein in the glass micro bead first phase maintains essentially all of the biological activity of the protein as it exhibited before the protein composition was processed into the first glass bead micro phase. Other processes for dehydration of a protein, such as in lyophilization, unfortunately result in a loss in at least a portion of the biological activity of the protein.

The present invention has established conditions that allow protein solutions to be glassified into micro beads. Using the two-phase micro systems described herein, wherein one phase is provided as a micro droplet that dissolves in another relatively immiscible excess phase, one embodiment of this invention creates micro glass beads of protein in a reduced hydration state, but not one that dehydrates the protein to such an extent that it looses its ability to function upon reconstitution (as can be the case for lyophilization). The principle lies in the fact that water of hydration is bound to molecules in excess water, and the work to remove the water is represented by a hydration potential, P. Essentially the outer most water molecules are the easiest to remove while the inner most are the most difficult and the work to remove water goes exponentially with distance (d) from the native protein surface, as:

$$P = P_o \exp(d/\lambda_{hyd})$$

wherein $P_o$ is the limiting potential and $\lambda_{hyd}$ is the decay constant of approximately 1 Å to 2 Å. This work to remove water is balanced by the water-dissolving capacity of the second phase solvent. Thus, whilst the protein has a certain potential to bind water and the second phase solvent has a capacity to dissolve water, the extent to which the second phase solvent does in fact remove water from the protein depends on this balance of potentials, essentially the chemical potential of water on the protein and in the second phase solvent.

Decanol, a second phase solvent that will dissolve water to some extent, reduces the water content of a hemoglobin solution as a microdroplet, to the extent that all the bulk water is removed as the droplet dissolves in the decanol, and the protein solution dehydrates to a particle or bead. However, it is envisioned that the present processes and devices may employ any number of different alcohols in addition to decanol, including do-decanol, pentanol, etc. From the initial volume and initial protein concentration, the concentration of protein in the final glassified or glass bead can be calculated. This number can be compared to the initial state of hydration. Hemoglobin in excess water has 1800 water molecules/Hb, in the glass state produced by this process, the protein has ~800-1000 water molecules/Hb. This compares to the crystalline state where the #water molecules/Hb is ~180. Thus, decanol is able to remove some water of hydration but not all of it, producing a partially hydrated (or dehydrated) protein sample. This principle provides for the production of macromolecules in states of partial dehydration by making water in oil emulsions in second phase solvents that dissolve the excess water and have the capacity to remove the desired amount of the water of hydration, but not all of it.

Another embodiment of the present invention provides for the partial dehydration of matter using an aqueous/aqueous system. In this system, one aqueous phase contains the material to be partially dehydrated in one compartment. This compartment is separated by a selectively permeable membrane from a second phase solvent compartment. The second phase solvent compartment comprises a water-soluble and water-absorbing polymer. The polymer or other moisture-absorbing material may be further described as having a certain potential to remove bulk water in addition to some water of hydration from the material. Here, ions, (for example) and other small molecular weight solutes, may also flow into the polymer, and so there is an exchange of water and other dissolved solutes not excluded by the selectively permeable membrane.

The pore size of the semi-permeable membrane and the surface charge or hydrophobicity of the membrane separating the two phases will determine which solutes or suspended material can freely diffuse across the membrane and partition between the two solvent phases. In one embodiment, the membrane could have a pore size allowing molecules less than 10000 MW to pass freely while retaining and dehydrating larger molecules.

The invention is intended to constitute any process that partially dehydrates matter, based on the recognition that small molecules, macromolecules, particles, membrane capsules and cells can be placed in contact with second phase solvents (either organic or aqueous polymer solutions, as for example emulsions or across dialysis membranes, or in contact with water absorbing polymers), that then compete for water of hydration on the material to be partially dehydrated, thereby partially drying the material but not to the point of loss of activity, (biological, pharmaceutical, nutritional, cosmetic), and thereby preserving the material for subsequent rehydration and use. This process can comprise varied physical parameters including but not limited to temperature, pH, buffering capacity, and stabilizers.

In one embodiment of this process, the product that forms after the material has been processed may be described as particles, solid spheres, and/or beads, particularly microbeads and/or nano-beads. Molecules like albumin and hemoglobin are demonstrated by the present inventors to readily form hydrated glasses (as opposed to crystalline states which are largely devoid of bound water). As discussed herein, in bulk aqueous solution, a protein like hemoglobin is in excess water, and the number of water molecules associated with each protein molecule is on the order of 1800 water molecules/hemoglobin (Hb). These water molecules are referred to as water of hydration, and represent water that is more or less bound and associated with the protein. Each water molecule may rapidly exchange with the bulk water but the net associated water is 1800/molecule Hb.

The second phase suspending solvent essentially sets the ultimate hydration state of the protein by its own ability to dissolve and partition water. Thus equilibrium is set up between the suspending phase, (for example a long chain alcohol, like decanol) and the aqueous protein solution micro droplet (emulsion) such that excess water readily dissolves in the solvent until the chemical potential of water is equal in the two phases. At this point the protein solution can have lost enough water such that the protein solidities as a glass state, with its level of hydration being set by the relative chemical potentials of water in the solvent and protein solution.

Since the degree of hydration of a given material, and in particular a protein, is set by the water potential in the solvent. Proteins may be more or less hydrated by choosing a solvent that has the capacity to dissolve more or less of the water of hydration (over and above the excess water), or by adjusting the relative volumes of the two phases.

One aspect of the processes described herein provides for the removal of a sufficient amount of water such that bacteria no longer can grow, while maintaining enough water of hydration such that the preserved (for example, in its glassified form) protein retains its biological and/or pharmacological activity, and may be readily reconstituted by the re-addition of excess water and separation of the two phases.

Process for Preparing Glassified Hemoglobin: In one aspect, the invention provides a process wherein a biological material of interest is partially dehydrated. This process may be defined in one example, and not by limitation, as comprising the following steps. First, a water solution of the protein, such as hemoglobin, to be glassified is to be prepared at fairly high protein concentration relative to its ultimate glassified state. This will reduce the amount of excess water that has to be removed before the bound water is removed. The protein solution is then to be gently suspended in the excess non-aqueous solvent to form a simple water in oil emulsion. Particle size can be about 2-30 microns with gentle shaking. The emulsion is stabilized against coalescence by the inclusion of small amounts (few millimolar) glycerol mono-oleate. The non-aqueous solvent is in sufficient excess to absorb all the free water from the protein solution (for decanol this is 100:1 while for pentanol it is 10:1), and allow the excess water to partition in to the non-aqueous phase. The emulsion thus dissolves in the non-aqueous phase and the droplet size reduces until the beads form.

The extent of dehydration is therefore set by the chemical potential of water in the non-aqueous solvent relative to the protein glass. Each micro droplet will then form the glass state and sink to the bottom of the suspension. Decanting the excess non-aqueous phase then allows the glassy protein beads to be stored until they are required for subsequent function. At this point excess aqueous buffer is added and mixed, causing each bead to coalesce with the aqueous interface and release its protein contents into the aqueous phase. The non-aqueous phase (decanol) either forms an emulsion or bulk phase that floats to the top of the suspension, leaving the protein in the infranate that can be drawn off through the tap of, say, a small syringe.

This process can be used to preserve (glassify or crystallize) any macromolecule, ionic compound, drug, vaccine or protein-rich material, or aqueous-soluble, non-aqueous insoluble composition, be it organic, inorganic or biological in nature.

EXAMPLE 2

Process for Dehydrating Cellular and Other Partially Hydrated Materials

The present example demonstrates the utility of the present invention for processing cellular components using a process that avoids the contact of the cellular component with any dessicant and/or absorbing materials, such as moisture absorbing polymeric materials, solvents, or other chemical materials. This is accomplished through the use of a system wherein moisture and/or liquid is drawn out of the cellular material composition though a selectively permeable membrane. By way of example, the cellular component to be examined here are red blood cells (RBCs), platelets and fresh frozen plasma.

Whole blood is typically collected into bags containing one of three anticoagulant-preservative solutions, CPD, CP2D or CPDA-1. The function of these solutions is to provide buffer, reduce free calcium, and provide energy sources for metabolism. Whole blood is then fractionated into red blood cells (RBCs), platelets and plasma. After removal of these components, an additive solution (AS-1, AS-3, or AS-5) is added to the remaining RBCs to restore the volume and adjust the hematocrit (AABB Technical Manual, 1999, Chapter 8: Blood Component Preparation, Storage, Shipping, and Transportation, pp 161-166). Using isolated RBC units, platelets, pooled plasma, and/or phereses platelets, the presently described processes may be used to reduce the water activity level of the unit, and thereby improve the shelf life and/or quality (reduced degradation of activity) of the component for future use.

Platelets are typically prepared by one of two methods. Platelet concentrates are prepared from units of whole blood that have not been cooled below 20° C. The RBCs are separated from the platelet-rich plasma within eight (8) hours after phlebotomy and the platelets are separated from the plasma by an additional centrifugation within twenty-four (24) hours. Platelet concentrates contain >$5.5 \times 10^{10}$ platelets in 40-60 ml of plasma (AABB Technical Manual, 1999, Chapter 8: Blood Component Preparation, Storage, Shipping, and Transportation, pp 173-174).

Platelets: Pheresis are platelets collected from single donors by aphaeresis. These components contain >$3 \times 10^{11}$ platelets in 100-500 ml of plasma and are the equivalent of roughly six units of platelet concentrate. Platelets must by stored refrigerated at a temperature of 20-24° C. under gentle agitation. Using conventional collection and storage techniques, the maximum storage time, depending on method of collection, is 5 days. Using the process described herein, the storage time is expected to be increased by at least 20%, and will be stored in a composition that has a characteristic water activity $a_w$ of about 0.3 to about 0.9, or at least less than 0.9 (See Table 1).

Figure 2:
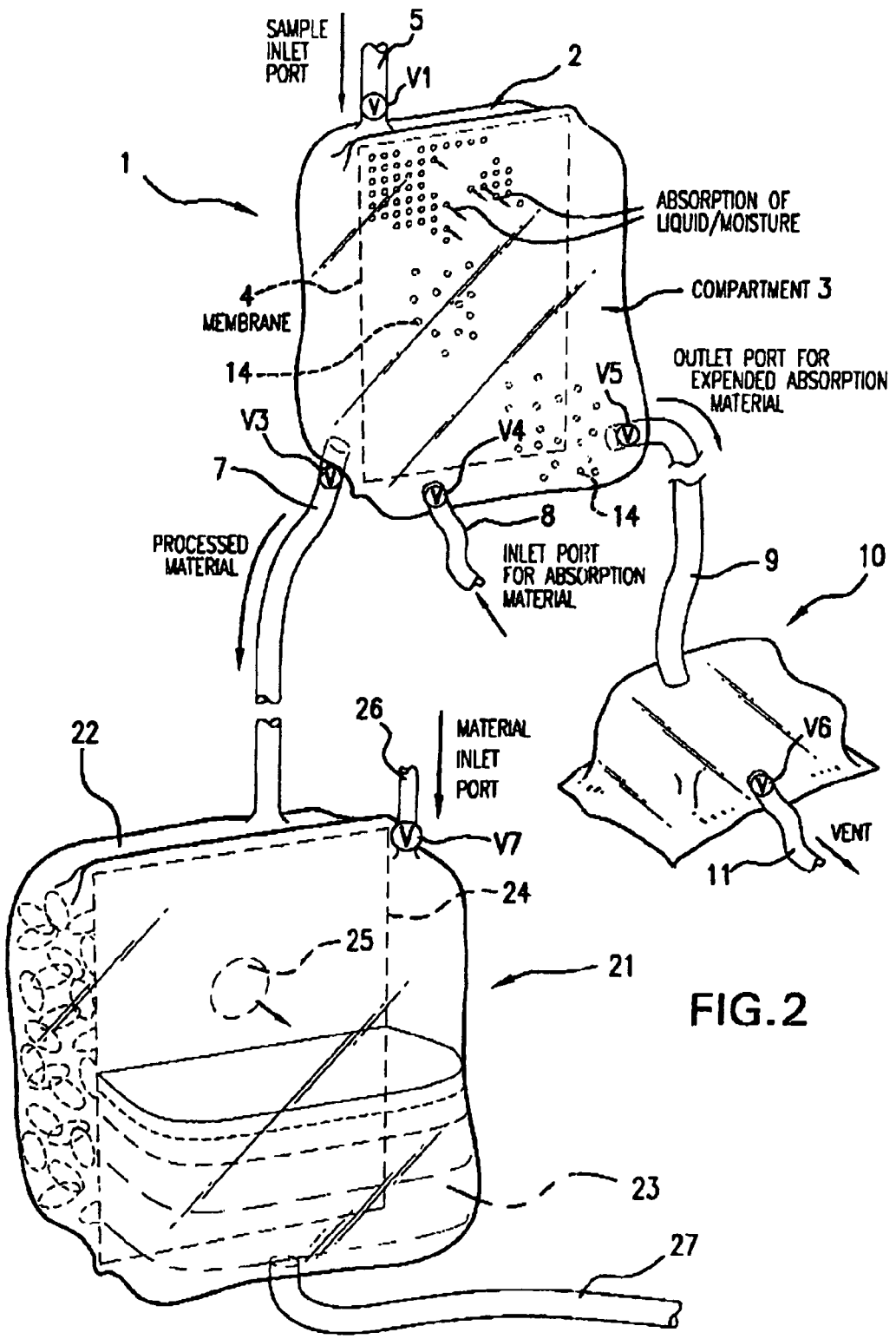
FIG. 2—Material Collection System and Device 2—Material compartment/bag (2), absorptive compartment (3), semi-permeable partition/membrane (4), inlet port A (5), inlet port B (6), outlet port C (7), inlet port (8), outlet port (for removal of expended absorbed material) (9). One-way valves (V) at inlet ports 5 (V1), inlet port 6 (V2), outlet port 7 (V3), inlet port 8 (V4), outlet port 9 (V5). Processed Product Storage and Reconstitution System 21, comprising a dehydrated material compartment/bag (22), diluent compartment (24), separating partition (25), inlet port D (28), outlet port E (27) (for removal of processed material), inlet port F (26). One-way valves (V) at inlet ports 26 (V7) and at outlet port 27 (V8).
Figure 3:
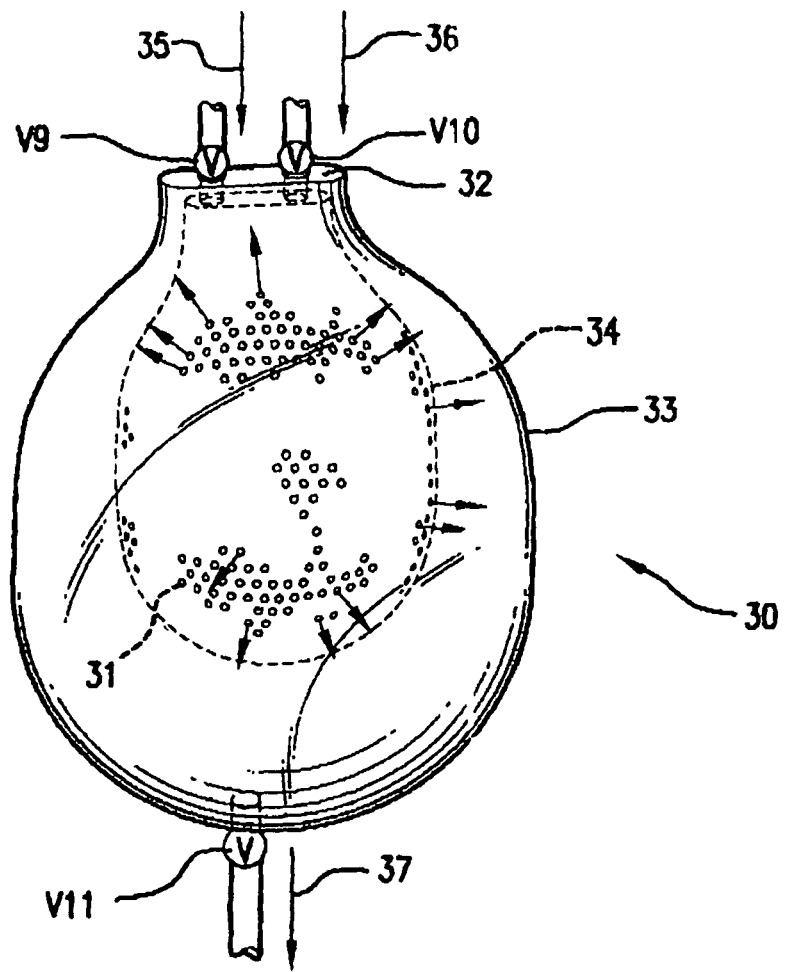
FIG. 3—Bag-in-a-Bag (Balloon-in-Balloon) Configuration of Processing Device (30). Sample compartment (34), Inlet port (35), having a one-way valve (V9) (for the input of sample to be processed), inlet port 36 having a one-way valve (V10) (for input of diluent into compartment 35), semi-permeable membrane having pores (31), moisture-absorbing compartment (33), outlet port 37 having a one-way valve (V11). Device top 32 with one or more fittings to accommodate inlet port 35 and inlet port 36.
Figure 4:
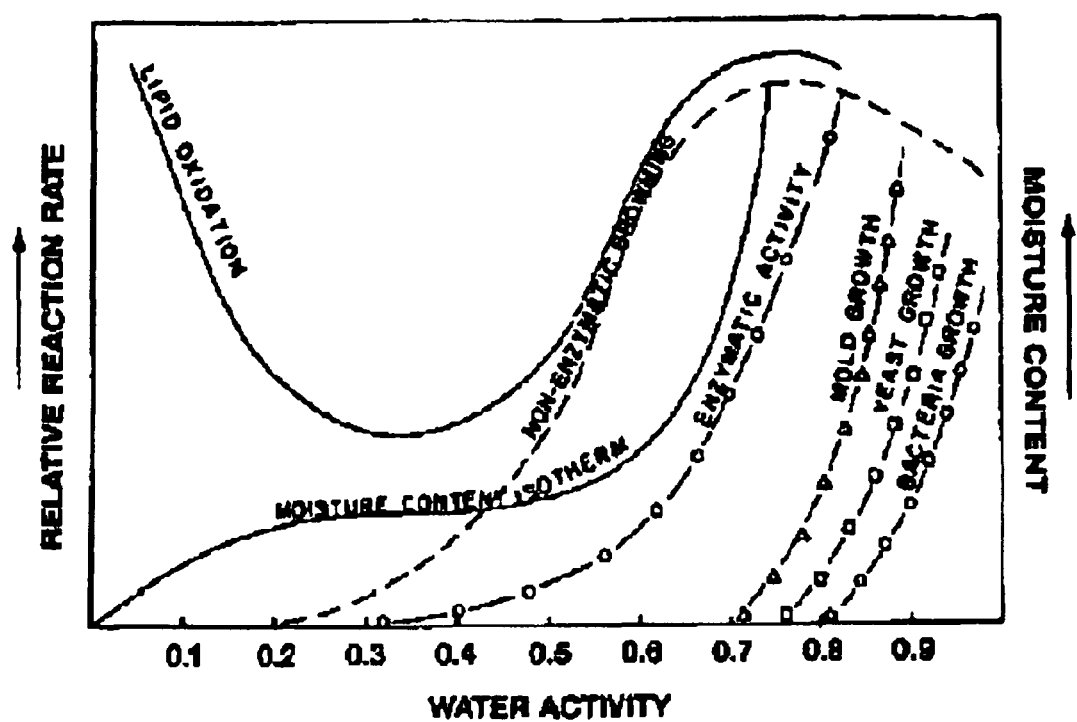
FIG. 4—Graph demonstrating water activity ($a_w$) and the relative reaction rate profiles of microbial growth (mold growth, yeast growth, bacterial growth) and enzymatic activity as a function of moisture content. Lipid oxidation and non-enzymatic browning, as well as the moisture content isotherm are also shown.

Red blood cells (RBCs) are partially dehydrated and stored using the process of Collection System I, wherein the moisture and/or liquid in the RBC unit is removed and/or reduced by not contacting the desiccant/absorbing material with the RBCs. Using the described system herein, and processing a separated unit of RBCs from a whole blood unit, it is expected that the storage life of the RBCs will be increased by at least 20%, and certainly be greater that the current shelf life of 42 days. According to the method of the present processes, a unit of RBCs will be placed in the device as depicted in FIG. 1, 2 or 3, and the water of hydration present in the cells reduced through the removal of said water/moisture component through a water permeable membrane. This action will provide a unit of processed red blood cells having a water activity level of less than about 0.9, or about 0.3 to about 0.9. (See Table 2).

Fresh Frozen Plasma: The major blood product component prepared from plasma are Fresh Frozen Plasma (FFP), Pooled Plasma, Solvent/Detergent-Treated Plasma, and Cryopre-cipitated Plasma (AHF). FFP and Pooled Plasma, Solvent/Detergent Treated Plasma may be stored at −18° C. for up to one year. Units collected and stored using conventional techniques and stored in this nature must be thawed at 30-37° C. and used immediately, or may instead be stored at 1-6° C. for no more than 24 hours prior to use (AABB Technical Manual, 1999, Chapter 8: Blood Component Preparation, Storage, Shipping, and Transportation, pp 170-172).

Using the presently described process, a unit of plasma, either pooled plasma or other form, would be treated so as to remove a sufficient level of hydration of the product so as to provide a plasma product having a stored water activity of at least 0.9 or less. It is anticipated this may be accomplished using the method as described herein, whereby the water/moisture component present in a conventional unit of plasma is drawn out by placing the plasma into a compartment of the presently described devices), and permitting the moisture and/or water component of the plasma to be drawn out of the plasma through a semi-permeable membrane. The reduced water activity (aw) plasma is then preferably stored in this partially dehydrated form until use. In this manner, preservation of the plasma is achieved without exposure of the sample to any chemical or desiccating material, and is isolated within the sterile compartment of the device until needed for use. Thus, the plasma product is anticipated to posses a greater shelf life than convention plasma products, of more than 12 months in the case of frozen plasma, and greater than 24 hours in the case of thawed plasma, and to be amenable to storage conditions that do not require as low temperatures as is typical for these products (See Table 3). In addition, it is anticipated that the activity of coagulation factors in the plasma unit will be better preserved during storage using the described techniques.

TABLE 1

Properties of Dehydrated Platelets compared under Current Standards Properties of dehydrated platelets

| Product Properties | Platelets | Platelets, Pheresis | Platelets, dehydrated Extended shelf life | Refrigerated | Frozen | Improved quality |
|---|---|---|---|---|---|---|
| Storage Life | 1-5 Days | 5 days | >5 days | >5 days | >5 days | 5 days |
| Storage Temp | 20° C. | 20° C. | 20° C. | 1-6° C. | <−18° C. | 20° C. |
| Storage Quality | storage lesions | storage lesions | same | same | same | reduced |
|  | Bacterial contam. | Bacterial contam. | same | same | same | reduced |
| Water activity($a_w$) | >0.9 | >0.9 | 0.3-0.9 | 0.3-0.9 | 0.3-0.9 | 0.3-0.9 |

TABLE 2

Properties of Dehydrated RBCs compared with Current Products

| Product Properties | Current standard RBCs Additive Solutions | Improved Compositions RBCs, dehydrtaed Extended Shelf Life | Increased Storage Temp. | Improved Quality |
|---|---|---|---|---|
| Storage Life | 42 Days | >42 Days | 42 Days | 42 Days |
| Storage Temp. | 1-6° C. | 1-6° C. | >6° C. | 1-6° C. |
| Storage Quality % Viability | >85 | >85 | >85 | >85 |
| pH | 6.5-6.6 | 6.5-6.6 | 6.5-6.6 | 6.7-7.2 |
| ATP % Initial Value | <70 | <70 | <70 | <70 |
| 2.3-DPG % | <10 | <10 | <10 | >10 |
| Water Activity | >0.9 | 0.3-0.9 | 0.3-0.9 | 0.3-0.9 |

TABLE 3

Properties of Dehydrated Fresh Frozen Plasma Compared to Existing Products

| Product Properties | FFP | FFP Thawed | Plasma, dehydrated (elevated storage temp) | Improved Shelf Life | Improved Quality |
|---|---|---|---|---|---|
| Storage Life | 12 mos | 24 hrs | 12 mos | 24 hrs | 12 mos | >24 hrs | 12 mos | 24 hrs |
| Storage Temp. | −18° C. | 1.6° C. | −18° C. | >6° C. | −18° C. | 1.6° C. | −18° C. | 1.6° C. |

TABLE 3-continued

Properties of Dehydrated Fresh Frozen Plasma Compared to Existing Products

| Product Properties | FFP | FFP Thawed | Plasma, dehydrated (elevated storage temp) | | Improved Shelf Life | | Improved Quality | |
|---|---|---|---|---|---|---|---|---|
| Storage Quality of Coag. Factors | Stable activity | Reduced activity | Same | Same | Same | Same | Same | Stable activity |
| Water Activity | >0.9 | >0.9 | 0.3-0.9 | 0.3-0.9 | 0.3-0.9 | 0.3-0.9 | 0.3-0.9 | 0.3-0.9 |

EXAMPLE 3

Multi-Compartmentalized Perishable Material Collection and Storage Preservation Device The present example is provided to demonstrate several of the numerous embodiments of the multi-compartment perishable material collection and storage/preservation device of the invention.

In some embodiments of the device, a closed system is provided in which the processed (partially dehydrated, reduced water viscosity product) food or biological product is maintained in the first compartment of the device, and upon the time the product is to be infused or used in a patient or consumed in the case of a food product, an appropriate rehydrating fluid, such as a sterile physiological saline (in the case of red blood cells) or consumable liquid, such as water or other liquid (water, etc.) is added in an appropriate amount to the first compartment through a port leading into this first compartment. The now rehydrated product may then be used as appropriate.

In a second embodiment of the multi-compartment perishable food, pharmaceutical or biological material collection and/or storage device, an additional component is included wherein the partially dehydrated and processed material is transferred to a product storage container. The second storage container will be fitted with an input outlet into which processed dehydrated material may be introduced therein, as well as an outlet port from which the reconstituted (i.e., rehydrated) material may be expelled for later use. The product storage container may also include an inlet port attaching the compartment to an adjacent storage compartment. This storage diluent compartment will contain a sterile saline solution and/or additives, in the case of blood components, or sterile water or other suitable liquid. This liquid component of the storage diluent compartment will then be infused into the second storage container and the product rehydrated as appropriate for use. In some embodiments, the second storage diluent compartment will be connected by a tubing and/or valve suitable for permitting the flow of the liquid/diluent into the second storage compartment containing the dehydrated perishable material.

As will be appreciated by those of skill in the art, the present description is exemplary in nature, and is not in any way intended to limit the scope or utility of the presently described devices and methods.

Collection System 1:

The presently described multi-compartmentalized biological sample unit is intended for particular application in the collection, storage and preservation of food products, pharmaceuticals, and biological products. By way of example, some such biological products include blood or blood component products, such as platelets, red blood cells, or particular components or fractions thereof.

In some aspects, the configuration of tile device (1) will comprise an arrangement as depicted herein at FIG. 1, by way of example and not limitation. In this example, the device comprises a plastic or other flexible and sterilizable material, such as cellulose acetate. In this configuration, the device will comprise a first compartment separated by a membrane from a second compartment. The second compartment will preferably contain a moisture absorbing material. The membrane will further comprise a series of pores therein, and may comprise the entire surface area that partitions the first compartment from the second compartment (such as in the balloon-in-balloon configuration depicted in FIG. 3), or may instead only comprise a portion of the surface area of the partition that separates the first compartment from the second compartment.

In some embodiments of the device, the top of the first container/compartment bag may be configured with three inlet/outlet ports. One inlet/outlet port provides for the transfer/input of the cellular elements; a second provides for diluent and/or additive input; and the third port acts as an outlet port for administration/infusion of the reconstituted product (See FIG. 1).

Collection System 2:

In a second embodiment of the perishable material collection system, the processed, partially dehydrated stabilized material having a reduced water activity ($a_w$) is expelled from the primary device container into a connected and separate storage container. This storage container has attached to it a liquid storage compartment within which is preferably contained an appropriate consumable diluent solution. (See FIG. 2).

In some embodiments of the device, a closed system is provided in which the processed (partially dehydrated, reduced water viscosity product) food or biological product is maintained in the first compartment of the device, and upon the time the product is to be infused or used in a patient or consumed in the case of a food product, an appropriate rehydrating fluid, such as a sterile physiological saline (in the case of red blood cells) or consumable liquid, such as water, is to be added in an appropriate amount to the first compartment through a port leading into this first compartment. The now rehydrated product may then be used as appropriate.

Both of the described Collection System 1 and Collection System 2 include a first compartment that is separated from the second compartment by a semi-permeable membrane or series of membranes. The semi-permeable membrane, in some cases described as a water permeable membrane, can be prepared and/or constructed from any variety of commercially available and suitable materials. By way of example, the semi-permeable membrane may comprise cellulose acetate, polysulfone, polyacrylonitrile, or other like material having a pore size with a molecular weight cutoff of about 1,000 to about 50,000. One determinant of the molecular weight cut off selected will be the molecular weight of the liquid absorbing material included within the desiccant containing compartment 3 of the device. A material should be selected that will not permit the liquid absorbing material to pass out of the compartment 3 into the compartment 2 of the device. As such, the liquid absorbing material will not come into contact with the perishable food or biological material being processed.

The lack of contact of the water absorbing material with the cellular material is an important advantage of the presently described processes in that, among other things, the water absorbing material (such as PEG polymer) will not be permitted to interact with the cellular material or other types of material being processed. In the case of biologicals, for example, it is well known that PEG can induce cell fusion, which would be highly undesirable and render a cellular material undesirable for use as a patient product.

By way of example, cellular elements that may be processed according to the present methods include those of mammalian origin, such as red blood cells, platelets, stem cells, food products, cells of other tissues, etc.

In a specific example of the invention, the configuration of the device is provided as a bag-in-a-bag (balloon-in-balloon) configuration (See FIG. 3). In one aspect, this embodiment may be described as a basic plastic bag having a volume of approximately 600 ml to 1000 ml. The plastic is a multi layer co-extruded high gas barrier film containing ethyl vinyl acetate and ethylene vinyl alcohol as gas and a water vapor barrier layer. The film is manufactured by blown extrusion in a class 10,000 clean room. Inside the primary bag is a secondary bag having a volume of approximately 300 ml to 500 ml. In some embodiments, this secondary bag is made from cellulose acetate. By way of example and not limitation, the secondary bag may contain approximately about 10 gm to about 30 gm of powdered crosslinked polyacrylic acid/polyalcohol grafted copolymer or other suitable polymer. The polymer selected should preferably be capable of absorbing approximately 20 times its weight of liquid. Within five to thirty minutes, the polymer will absorb liquid forming a gel within the cellulose acetate bag; leaving the cellular elements in a dehydrated state. The dehydrated elements can be subsequently reconstituted using an appropriate diluent when infusion of the elements is desired.

In some embodiments, the bottom of the bag will contain an integrally sealed cellulose acetate bag with an inlet port for filling of the dried polymers, and a tertiary bag having a volume of approximately 300 ml. to 500 ml to permit purging the polymer gel out of the system. The tubing to the tertiary bag will contain a one-way check valve (V) to prevent gel reflux back into the primary bag, and to avoid primary bag re-entry. The tertiary bag may then be sealed and discarded to allow minimal weight and maximal logistical flexibility.

The finished product may be gamma ray sterilized.

EXAMPLE 4

Semi Permeable Membranes

The ability of a molecule to pass through a particular barrier, such as a moisture permeable membrane, is determined by the size of the pores in the membrane, referred to as the pore size. Where the pore size of the membrane is 10 nm, then a molecule with the smallest dimension greater than 10 nm will be retained with 100% efficiency. In practical terms, the retention with 100% efficiency is usually not possible. The term molecular weight cutoff (MWCO) is commonly used. The MWCO defines the molecular weight of a molecule that is retained with 90% efficiency. A variety of moisture permeable and semi-permeable membranes with various MWCO, for example 2K, 3K, 4K, 5K, 6K, 7K, 8K, 9K, or 10K, may be used in the practice of the present inventive devices and processes, and are commercially available.

Molecules diffuse from high concentration to low concentration until equilibrium is reached. When two compartments are separated by a semi-permeable membrane, only those molecules that are small enough to fit through the membrane pores are able move through the membrane and reach equilibrium. Large molecules that cannot pass through the membrane pores will remain on the same side of the membrane, as they are too large to pass through the pores of the semipermeable membrane.

The semi permeable membrane can be made of various materials including but not limited to, cellulose nitrate, mixed cellulose ester, cellulose acetate, nylon, or polyethersulfone. The choice of specific material is determined by various factors including but not limited to strength, wetting properties, flow rates, static charge, aqueous extractability, solvent resistance, hydrophilicity/hydrophobicity, and protein binding.

EXAMPLE 5

Dehydration of Viruses

The present example demonstrates the utility of the present invention for the processing and storage of viruses.

Many viruses are used as vaccines. These viruses are generally preserved by lyophilization if possible. If lyophilization is not practical, the viruses must be stored in aqueous suspension and kept frozen or refrigerated. The necessity of the cold-chain distribution system adds cost and complexity to the distribution process. Therefore, methods of dehydrating these compositions without destroying their biological activity are needed.

Since these viruses cannot be directly contacted with desiccating solvents, it is necessary to avoid contacting the desiccant with the virus particles. This can be accomplished by maintaining the virus particles in an aqueous suspension in a compartment separated from a second compartment by a semi permeable membrane.

The second compartment contains a desiccant capable of withdrawing water from the aqueous phase in the first compartment. The desiccant can be taken from a group of compounds including but not limited to PEG and polyacrylamides. The semi permeable membrane can be dialysis membrane or any selectively permeable membrane that is permeable to water but retains the virus particle.

EXAMPLE 6

Multi-Well Titer and Assay Plates Having Processed Biological Material

The present example demonstrates the utility of the present invention for the preparation of multi-well assay and titer plates, such as those useful in typical diagnostic and clinical applications.

Standard 96-well plates are used for numerous laboratory and quality control applications. Such a multi-well plate may be prepared to include many different partially dehydrated biological materials prepared according to the present invention. These biological material compositions are present in a dehydrated state, and therefore present a significant advantage for long-term storage purposes and for purposes of ready availability without the necessity of adding assay and/or test material to each well upon use. It is difficult to deliver many of these compounds to a multi-well plate such that they are stable. In some embodiments of the invention, the multi-well plate may be prepared by first adding a desiccant and/or moisture absorbing material to the bottom of each well, and then covering the wells with a moisture/water permeable membrane. The desired liquid-containing composition (biological material) in aqueous solution or suspension may then be added to each well.

On the opposite side of the semi permeable membrane is a desiccant such as PEG or polyacrylamides capable of drawing water out of the aqueous phase through the membrane. This will result in an in situ dehydration of the desired material in the well. The size of retained, dehydrated material is determined by the pore size of the selectively permeable membrane thereby used to separate the two phases.

EXAMPLE 7

Transdermal Drug Delivery

The present example is provided to demonstrate the utility of the present invention for the preparation of transdermal drug delivery devices that include the preserved biological materials described herein. By way of example, the transdermal device may be prepared to include the following partially dehydrated biological materials: nitroglycerin, estrogen, progesterone and testosterone.

Devices are currently in use and development for transdermal drug delivery. These devices require that the drug be deposited on the delivery matrix in a dehydrated form. The deposition of a drug glass can be accomplished by using a layer of the transdermal drug delivery matrix covered with a layer of the drug in aqueous solution or suspension, covered with a water permeable membrane, and with a final layer of desiccant on the opposite side.

EXAMPLE 8

Dry Injection Devices

The present example is provided to demonstrate the utility of the present invention for the preparation of injectable preparations, such as insulin, vaccines, or other biological preparations employing the partial dehydration technologies of the present disclosure.

By way of further explanation and clarification, and not limitation as to mechanism of action, one of the principles underlying the present technology is that particles of solid-form drugs can be painlessly delivered into the body at high efficiency traveling at a high velocity. These drugs may be therapeutic agents or vaccines and may be small molecules, peptides, proteins or genes. The technique can be applied using the appropriate injection system to deliver any drug formulated as a solid particle of the appropriate size, mass, density and strength through the skin, the tissues of the mouth and other routes.

When the delivery mechanism is activated, it opens a gas canister, which allows helium gas at high pressure to enter a chamber at the end of which is a drug cassette containing the powdered drug between two plastic membranes.

At the designed release pressure, virtually instantaneous rupture of both membranes causes the gas to expand rapidly, forming a strong shock wave, which travels down the nozzle at speeds of 600-900 meters per second. Behind this shock wave is the initial gas flow, which carries the drug particles, accelerating them to a speed approaching 750 meters per second. As the shock wave, followed by the helium gas containing the drug particle, leaves the nozzle and hits the skin surface, the drug particles have sufficient momentum to penetrate the skin while the helium gas is reflected into a silencer.

Individual tiny particles of drug powder pass through the outer layer of the skin tracking down to the required level of penetration in the tissue. The drug dissolves and then either acts locally or diffuses into the bloodstream to deliver its therapeutic effect.

The technology to achieve dehydration of these drug particles is described in the preceeding examples provided herein.

EXAMPLE 9

Hemostatic Agent and Wound Sealant

The present example is provided to demonstrate the utility of the present invention for the preparation of partially dehydrated would sealants, such as fresh frozen plasma (FFP) biological components.

Because of the very high concentrations of coagulation factors in FFP, it is envisioned that given the correct concentration of the dehydrated material, FFP could be used as an external or internal wound-sealing product similar to the fibrin sealants currently being marketed commercially.

In one embodiment, the wound sealant is formed in situ and comprises autologous plasma. A device designed to collect and concentrate a patient's own plasma either directly at the site of the wound or via prior collection and dehydration is possible. A device is also envisioned that would be a bandage comprising a selectively permeable membrane separating a compartment containing a dehydrating material. This bandage would be applied directly to the wound and would withdraw water while concentrating the cellular and plasma constituents of blood responsible for clotting and coagulation. The resulting concentrated factors could be further activated by adding agents such as calcium to the bandage. The methods employed in the above mentioned examples can be employed to construct such a device.

EXAMPLE 10

Rehydration of Processed Biological Materials

The present example demonstrates the utility of the present invention for preserving essentially all of the biological activity of a biological material processed according to the present invention. The present example also demonstrates the method, by way of example and not exclusion, that a biological material processed according to the present techniques, can be rehydrated for use in a patient.

These factors demonstrate the advantages to be achieved employing fresh frozen plasma and the herein described processes of partial dehydration for processing FFP for subsequent clinical use.

Current standards for RBCs collected in CPD, CP2D, or CPDA-1 must have a hematocrit of less than 80%. AS-RBCs contain an additive solution and are generally ill the range of 55-65%.

The dehydrated RBCs are rehydrated to a hematocrit of 50-80% prior to transfusion. The exact hematocrit should be determined taking into account patient fluid volume requirements. A patient with the potential for volume overload would preferably receive a unit with a higher hematocrit.

The solution used to rehydrate the dehydrated RBCs should be an agent approved by the FDA for i.v. (intra venous) administration to humans. The preferred solution would be physiological saline. The amount added should be sufficient to attain the desired hematocrit. The hematocrit can be determined by labeling instructions on the dehydrated RBC storage bag or can be determined by measuring the hematocrit immediately prior to dilution.

EXAMPLE 11

Processing of Perishable Food Products

The present example is provided to demonstrate the utility of the invention for the preservation and preparation of food products.

The concept of water activity has been studied for decades and used extensively in the food industry as a method of preservation. The concept has had limited use in pharmaceutical and biological applications. One major reason for this is the necessity to lower water activity by adding compounds to the material being dehydrated. While this is possible with many food substances, it is not feasible for certain foods and most pharmaceutical agents especially those not administered by all oral route.

A key to stabilizing and preserving a biological agent is to reduce enzymatic activity. This can be accomplished by many means the most common being cooling or freezing. The same can be accomplished by reducing water activity. This has been studied extensively in the food industry.

A key consideration in the preparation of various compositions by the invention is the reduction in the potential for the growth of pathogenic or other microbial agents. The relationship of water activity to microbial growth has been studied extensively for many microbial agents including human pathogens. The water activity of various compounds has been determined. The compounds of interest in the current invention are those that are immiscible in water or those that are of sufficiently high molecular weight so as to be impermeable to a semi-permeable membrane. References on the water activity of various compounds are provided.

There are many examples of humectants that are commonly used in the preparation of intermediate moisture foods. Table 4 shows that solutes such as sorbitol can have significant effects on water activity. At maximum solubility of 70% w/v, sorbitol reduces the water activity to 0.79. Since pathogenic bacteria do not grow below a water activity of 0.86, this would act as a preservative. Such an approach, however, is not useful for the preservation of biological materials such as platelets. The addition of this amount of sorbitol to a suspension of platelets would render them useless for use in humans.

Intermediate moisture foods generally have a water activity in the range of 0.6-0.9. This water activity is attained by adding a solid water binder, a solute, partial drying, or a combination of these. Drying methods commonly used employ either heat or vacuum to remove water. The other methods involve adding either a solid water binder or a solute to the food.

The process described in the current invention involves the use of a solid water binder or a solute to remove water. However, it is novel and distinct from the currently used methods in that the agent used to remove water and reduce water activity does not come into contact with the food being dehydrated. The requirement to add the drying agent directly to the food can alter the taste and texture of the food as well as pose potential safety risks due to potential toxicity of the drying agents. The current invention totally eliminates this by separating the food with a semi permeable membrane from the drying agent which is impermeable to the membrane. A device with a configuration similar to those used for the drying of blood components. There are two compartments separated by a semi permeable membrane. One compartment contains the food that is to be partially dehydrated. The second compartment contains a dehydrating agent that is not permeable to the semipermeable membrane and is present in sufficient quantity to reduce the water activity of the food to the desired level. The temperature is maintained in a range where the food is not frozen. The optimal temperature is determined by assessing organoleptic and other critical properties such as nonenzymatic browning and lipid oxidation.

TABLE 4

Common solutes and their properties for reducing $a_w$

| Solute | Maximum solubility in water (%) | of saturated solution $a_w$ |
| --- | --- | --- |
| Lactose | 20 | 0.97 |
| Glucose | 47 | 0.92 |
| KCI | 27 | 0.86 |
| Sucrose | 69 | 0.86 |
| Sorbitol | 70 | 0.79 |
| NaCl | 26 | 0.75 |
| Fructose | 75 | 0.63 |
| Glycerol | 100 | 0.00 |

Labuza, T. P. (1984) Moisture Sorption: Practical Aspects of Isothenn Measurement and Use, AACC

BIBLIOGRAPHY

The following references, articles, patents and publications are specifically incorporated herein by reference where appropriate for appropriate teachings of additional or alternative details, features, and/or technical background.

AABB Technical Manuel, 2001;

"Remington: The Science and Practice of Pharmacy", A. Gennaro (June 2003). ISGN:0781750253.

Goodman & Gilman's. The Pharmacological Basis of Therapeutics, Hardman, Limbird, Gilma (August 2001), USBN: 1354697.

"Drug Facts and Comparisons, 2004", ISBN: 157439178X.

Bone, D. 1969. Water activity: Its chemistry and applications. Food Prod. Dev. August. 3(8):81.

Acker, L. 1963. Enzyme activity at low water contents. Recent Adv. Food Sci. 3:239.

Acker, L. (1969), Water Activity and Enzyme Activity, Food Technol. 23:1257.

Fisher, H. F. (1965), Hydration of a Protein Molecule, Biochim. Biophys. Acta., 109:544.

Fogiel, A., and W. Heller. (1966), Sorption of Vapors by Protein. J. Phys. Chem., 70:2039.

Christian, J. (1963), Water activity and growth of Microorganisms, Recent Adv. Food Sci. 3:248.

Labuza, T. P. (1984) Moisture Sorption: Practical Aspects of Isotherm Measurement and Use, AACC Loncin, M., J. Bimbenet and J. Lenges. (1968), Influence of the Activity of Water on the Spoilage of Foodstuffs, J. Food Technol., 3:131.

Scott, W. (1957), Water relations of food spoilage microorganisms, Adv. Food Res. 7:83, G. Stewart, ed. Academic Press, New York.

Arai, C., S. Hosaka, K. Murase and Y. Sano. (1976), Measurements of the relative humidity of saturated aqueous salt solutions. J. Chem. Eng. Japan. 9(4):328-329.

Cakebread, S. H. (1972), Vapour pressures of carbohydrate solutions. Confec. Prod. 38:407-410.

Cakebread, S. H. (1972), Vapour pressures of carbohydrate solutions. II. Confec. Prod. 38:486-496.

Cakebread, S. H. (1972), Vapour pressures of carbohydrate solutions. III. Confec. Prod. 38:524-526, 550.

Cakebread, S. H. (1972), Vapor pressures of carbohydrate solutions. IV. Confec. Prod. 38:585-586, 604.

Cakebread, S. H. (1972), Vapour pressures of carbohydrate solutions, v. Confec. Prod. 38:638-640, 668.

Chirife, J., G. Favetto, C. Ferro Fontan and S. L. Resnik. (1983), The water activity of standard saturated salt solutions in the range of intermediate moisture foods. Lebensm. Wiss. Technol. 16:36-38.

Gal, S. (1968), The water vapor sorption isotherm of various sorbents. Chimia 22:409.

McLaren, A. P., and J. Rowen, (1952), Sorption of water vapor by proteins and polymers. J. Polymer Sci. 7:289.

Puffa, R., and J. Sebenda. (1967), The mechanism of water sorption in polyamides J. Polymer Sci. Polymer Symp. 16:79-93.

Sloan, A. E., and T. P. Labuza. (1976), Prediction of water activity lowering ability of food humectants at high aw. J. Food Sci. 41:532-535.

Sloan, A. E., D. Schlueter and T. P. Labuza. (1977), Effect of sequence and method of addition of humectants and water on aw lowering ability in an IMF System. J. Food Sci. 42:94-96.

U.S. Pat. No. 4,687,580—"Membrane Apperatus/Process Adopted for Plasmapheresis;

U.S. Pat. No. 4,326,959—"Blood Separation and Dispenser";

U.S. Pat. No. 4,921,473—Multicomponent Fluid Separation System;

U.S. Pat. No. 4,131,200—"Thromboplastic Blood Bags";

U.S. Pat. No. 4,921,473—"Blood Reservoir";

U.S. Pat. No. 4,976,708—"Blood Reservoir";

U.S. Pat. No. 4,994,021—"Apparatus and Method of Collecting and Freezing Blood Plasma";

U.S. Pat. No. 4,545,910—"Semi-Permeable Membranes";

U.S. Pat. No. 4,994,057—"Sterilization System for Blood Storage";

U.S. Pat. No. 4,185,629—"Method and Apparatus for Processing Blood";

U.S. Pat. No. 5,776,769—"Cell-Type Specific Methods and Devices for the Low Temperature Preservation of Cells of an Animal Species";

U.S. Pat. Re 34,239—"Semi-Permeable Membranes";

U.S. Pat. No. 5,750,330—"Method and Composition for Lyophilizing Red Blood Cells";

U.S. Pat. No. 5,888,408—"Process for Collecting and Preserving Stored Blood, Apparatus Suitable for Said Process and Use of the Apparatus";

U.S. Pat. No. 5,985,315—"Method of Preparing a Biological Glue able to Coagulate Simply by Addition of Calcium Ions";

U.S. Pat. No. 5,261,255—"Device for Fractionating Constituent Components of a Substance Using Cryoprecipitation";

U.S. Pat. No. 6,406,712—"Aqueous Gel and Package for a Wound Dressing Material";

U.S. Pat. No. 6,524,533—"Device for Collecting and Drying a Body Fluid";

U.S. Pat. No. 6,168,561—"Blood Processing Coulter Counter Balanced with Blood-Free Liquid";

U.S. Pat. No. 6,748,164—"Plasma Thawing System";

U.S. Pat. No. 6,582,349—"Blood Processing System".

What is claimed:

1. A composition comprising glassified, stabilized particles prepared in a water in oil system in the absence of a solvent phase separation enhancing agent, said particles having a water activity less than about 0.9 and comprising an active agent of a protein, antibody, peptide, hormone, polynucleotide, blood plasma, blood cells, viruses, food product, pharmaceutical product or cosmetic product.

2. The composition of claim 1 wherein the protein is an enzyme.

3. The composition of claim 2 wherein the protein is a blood protein.

4. The composition of claim 3 wherein the blood protein is hemoglobin, a clotting factor or factors, albumin, immunoglobulins, or a combination thereof.

5. The composition of claim 1 wherein the hormones are estrogens, progesterone, testosterone, or any combination thereof.

6. The composition of claim 1 wherein the polynucleotides are DNA, RNA, siRNA, mRNA, tRNA, plasmids, genes, oligonucleotides, or any combination thereof.

7. The composition of claim 1 wherein the glassified, stabilized particles of blood plasma are prepared from a fresh plasma sample or a previously frozen plasma sample.

8. The composition of claim 1 wherein the blood cells are white blood cells, red blood cells, platelets, or a combination thereof.

9. The composition of claim 1 wherein said glassified, stablilized particles are glassified, stabilized particles of a food product.

10. The composition of claim 1 wherein said glassified, stablilized particles are glassified, stabilized particles of a cosmetic product.

11. The composition of claim 1 wherein the glassified, stabilized particles have a size of 100 nm to 500 microns.

12. The composition of claim 1 wherein the pharmaceutical product is within a transdermal drug delivery device.

13. The composition of claim 1 wherein the pharmaceutical product is an injectable pharmaceutical product.

14. The composition of claim 1 wherein the pharmaceutical product is within a transdermal drug delivery device.

15. The composition of claim 12 wherein the transdermal drug delivery device is a patch suitable for adhesion to a skin surface.

16. The composition of claim 1 wherein said stabilized particles have a size of about 100 nm to 500 microns.

17. A wound treating agent comprising a glassified, stablilized particle composition as defined in claim 1, wherein said pharmaceutical agent is a therapeutic agent.

18. The wound treating agent of claim 17 wherein the agent is provided within a bandage, said wound treating agent comprising a wound sealant, growth factor, antibiotic, antiseptic, anticoagulant, or growth promoting agent.

* * * * *